United States Patent
Andraos

(10) Patent No.: US 9,228,865 B2
(45) Date of Patent: Jan. 5, 2016

(54) MULTI-ANALYZER AND MULTI-REFERENCE SAMPLE VALIDATION SYSTEM AND METHOD

(71) Applicant: Xenon, Inc., Irvine, CA (US)

(72) Inventor: Michael Paul Andraos, Irvine, CA (US)

(73) Assignee: XENON, INC., Irvine, CA (US)

(*) Notice: Subject to any disclaimer, the term of this patent is extended or adjusted under 35 U.S.C. 154(b) by 0 days.

(21) Appl. No.: 13/868,994

(22) Filed: Apr. 23, 2013

(65) Prior Publication Data

US 2013/0276507 A1 Oct. 24, 2013

Related U.S. Application Data

(60) Provisional application No. 61/637,168, filed on Apr. 23, 2012.

(51) Int. Cl.
| | |
|---|---|
| *G01N 35/04* | (2006.01) |
| *G01D 18/00* | (2006.01) |
| *G01N 33/28* | (2006.01) |
| *G01N 35/00* | (2006.01) |

(52) U.S. Cl.
CPC ............ *G01D 18/00* (2013.01); *G01N 33/2829* (2013.01); *G01N 35/00623* (2013.01); *C10L 2200/0423* (2013.01); *C10L 2290/60* (2013.01)

(58) Field of Classification Search
CPC .................. G01N 33/0006; G01N 27/4163
USPC ............. 73/1.02–1, 23.22–23.42, 863.31, 73/863.81
See application file for complete search history.

(56) References Cited

U.S. PATENT DOCUMENTS

| | | | | |
|---|---|---|---|---|
| 5,469,751 A | * | 11/1995 | Weiss et al. | 73/863.33 |
| 5,780,716 A | * | 7/1998 | Shimizu et al. | 73/23.2 |
| 2003/0000281 A1 | * | 1/2003 | Ketler et al. | 73/1.06 |
| 2003/0010140 A1 | * | 1/2003 | Kopl et al. | 73/863.31 |
| 2012/0260715 A1 | * | 10/2012 | Miyai et al. | 73/1.07 |

* cited by examiner

*Primary Examiner* — Eric S McCall
*Assistant Examiner* — Anthony W Megna Fuentes
(74) *Attorney, Agent, or Firm* — Sheridan Ross P.C.

(57) ABSTRACT

Validation systems and methods are described. Specifically, the disclosed validation system has the ability to simultaneously or sequentially analyze the Reid Vapor Pressure (RVP) or any other property of process samples taken from the same or different sources. The validation system is scalable to validate with multiple reference samples to one or multiple analyzers. The system is also scalable to operate multiple streams of a single or multiple fuels to multiple analyzers.

11 Claims, 5 Drawing Sheets

MULTI-ANALYZER AND MULTI-REFERENCE SAMPLE VALIDATION SYSTEM AND METHOD

CROSS REFERENCE TO RELATED APPLICATIONS

This Application claims the benefit of U.S. Provisional Application No. 61/637,168, filed Apr. 23, 2012, the entire disclosure of which is hereby incorporated herein by reference.

FIELD OF THE DISCLOSURE

The disclosure relates to sample validation systems and methods for operating the same.

BACKGROUND

There are significant economic credits associated with process optimization. Real time optimization and control is dependent on reliable online analyzers and a means to accurately quantify standard deviation and control to tighter specifications with confidence. Xenon's validation system is fully automated and scalable to initiate and control analyzer validations with known samples, including but not limited to process reference samples, Neohexane, N-Pentane, etc. The integral controller manages validation sequences and operates seamlessly with site process control systems. Analyzer validation sequences can be initiated automatically or manually by the operator as needed.

Validation and testing systems exist in many forms. Most validation systems are typically applied to a single process analyzer as an add-on feature offered by some OEMs for their own equipment. It is the validation system's responsibility to supply a reference sample to most analyzer at the same flow rates and pressures as normal process sample conditions to determine analyzer accuracy against a known reference value. In essence, the validation system is used to test a measuring device for accuracy without adjusting the analyzer's output. The deviation between the actual analyzer response and reference value is utilized by the process controller to normalize analyzer readings to optimize process control to exact specifications. Typical analytical properties validated include but not limited to Reid Vapor Pressure (RVP), Sulfur, Octane, Aromatics, Oxygen, miscellaneous gaseous and liquid processes.

RVP represents a fuel's evaporation at 100 degrees Fahrenheit and is measured in pounds per square inch (PSI). Since the property that RVP measures (evaporation rate) is often referred to as the fuel's volatility, it is clearly a property that is strictly monitored and controlled during the production of fuels. Indeed, fuel refineries, production facilities, transportation companies, and the like spend a great amount of time, energy, and capital analyzing fuel RVP at different stages of production.

The RVP for gasoline should always be below 14.7 PSI, which is normal atmospheric pressure. If the RVP is higher than 14.7 PSI, excess pressure will build and the fuel might boil and evaporate while in a car's gas tank. The Environmental Protection Agency (EPA) regulates RVP for gasoline purchased at retail gas stations during the summer months to help reduce emissions.

For crude oils, understanding RVP can help the oil companies more safely gather, refine, store and transport their products. Accordingly, many companies along the product chain for various fuels constantly analyze RVP for their fuels. Validation systems are commonly employed to test the accuracy and validity of the analyzers that perform the analysis of the process materials.

SUMMARY

It is one aspect of the present disclosure to provide a fully scalable multi-analyzer and multi-reference sample validation system and method.

In particular, embodiments of the present disclosure are directed toward systems and methods for multi-analyzer and multi-reference sample validation. The validation system may be applied to validate RVP analyzers, Gas Chromatographs, Sulfur Analyzers, Raman Analyzers and the like. Accordingly, although details of the present disclosure will describe details of an RVP validation system and method, it should be appreciated that the invention is not so limited. Rather, embodiments of the present disclosure are intended to cover any type of multi-reference sample validation system and methods of operating the same.

Multi-analyzer, multi-reference validation as disclosed herein can be likened to automatically supplying multiple references (e.g., reference samples) to a measuring device at predetermined values within its measuring capability. For example, embodiments of the present disclosure enable the ability to test linearity of an analyzer by supplying the analyzer with a reference sample at a low range and another reference sample at a high range. Based on the provided reference samples, the multi-reference validation system can determine the analyzer's accuracy across a spectrum (e.g., between the low range and high range) or at a single value.

In some embodiments, the multi-analyzer, multi-reference validation system may be utilized for providing two distinct and different reference samples to the same or multiple analyzers, either sequentially or simultaneously. As a non-limiting example, the multi-reference validation system may be configured to provide a first reference sample (e.g., N-pentane which is a readily available reference fluid with a known RVP value of 15.45) and then a second reference sample (e.g., Neohexane is another available reference fluid with a known RVP value of 9.6). Depending on what type of fuel a refinery is blending, they may prefer to use different references to compare the readings of the different analyzers. Alternatively or additionally, the site may elect to provide their own reference fluid with a known RVP value and validate the readings of the analyzer against that particular standard.

It is another aspect of the present disclosure to provide a validation system that is capable of performing a re-graph feature. This re-graph feature allows actual process sample to become its own "standard" by which future analyzer validations are compared. For instance, if the validation system is being applied on an RVP analyzer and the site can create their own reference fluid by utilizing the functionality of the multi-reference sample validation system. Upon initiation, the validation system can collect a sample of the process fluid (in this case, the gasoline in the blend header) and initiate analysis of the collected fluid by the online analyzers. The system will then store the averaged value of analysis as the "known" standard upon which future validations will be compared. The collected sample can then be stored in an external vessel that collects a set amount of reference sample so it can be used for future validations and it also has the ability to send the newly collected reference sample to a manual sample collection station, which allows the reference fluid to be collected in a sample bottle and analyzed by a laboratory.

It is one aspect of the present disclosure to provide a multi-reference sample validation system and method for operating the same that overcomes the above-noted deficiencies. The system may include one or more of RVP analyzers, chromatographs, sulfur analyzers, and the like. As a non-limiting example, it is one aspect of the present disclosure to provide an RVP validation system that is scalable to validate multiple RVP analyzers simultaneously or sequentially.

It is another aspect of the present disclosure to provide a validation system that is scalable to validate with multiple reference samples to multiple analyzers (e.g., RVP analyzers, chromatographs, sulfur analyzers, etc.).

It is another aspect of the present disclosure to provide a validation system that is scalable to operate multiple streams of a single or multiple fuels to multiple analyzers.

It is another aspect of the present disclosure to provide a validation system that includes an analyzer stream selection (process/validation) fully independent for each analyzer, for example: the system is designed to introduce process (e.g., fuel sample) to one analyzer cell while simultaneously isolating or introducing process/validation to the other analyzer cell.

It is another aspect of the present disclosure to provide a validation system that achieves substantially no cross-interference of validation samples, regardless of whether or not the validation samples have been taken simultaneously or sequentially from the same or different source.

It is another aspect of the present disclosure to provide a validation system that is capable of performing validation with gasoline and/or Neohexane and/or N-Pentane reference samples, sequentially or simultaneously.

It is another aspect of the present disclosure to provide a validation system that delivers consistent sample delivery to each analyzer cell for all streams (e.g., constant pressure and flow rates).

It is another aspect of the present disclosure to provide a controller (e.g., Programmable Logic Controller (PLC), microprocessor, Field Programmable Gate Array (FPGA), firmware, software, combinations thereof, etc.) that is capable of monitoring and controlling some or all of the operations performed by the validation system. All remote Distributed Control System (DCS) commands can be transmitted to the controller for final execution at the validation system.

It is another aspect of the present disclosure to provide PLC/HMI (e.g., user interface for PLC) control and system health monitoring to ensure reliable and repeatable sample analysis.

It is another aspect of the present disclosure to provide remote (DCS) and/or local (PLC/HMI) system operation. It should be noted that certain maintenance functions may benefit from only being capable of initiation locally from the PLC/HMI.

It is another aspect of the present disclosure to provide system status outputs to DCS, including common trouble alarms, which may operate independently for each analyzer cell.

It is another aspect of the present disclosure to provide the ability to auto re-graph a gasoline reference value upon refill of a fuel (e.g., gasoline) cylinder. The fuel reference re-graph cycle can be initiated remotely and/or locally.

In accordance with at least some embodiments of the present disclosure, a validation system is provided which comprises:
  a set of double block and bleed valves and three-way valves dedicated to each analyzer;
  pressure and flow instruments to ensure process and validation samples are supplied to the analyzers under stable and consistent conditions;
  solenoid-operated valves and interconnections operated by the controller for stream selection;
  constant pressure cylinders to contain reference samples;
  motive gas controls to operate pressure cylinders and air-operated valves; and
  a controller configured to independently manage operations and communications of the validation system In some embodiments, the first material under test may be a first fuel and the second material under test may be a second fuel. The first fuel may be the same as the second fuel and the first sample may be taken at a different time than the second sample. In some embodiments, the first sample and second sample may be simultaneously taken from the same fuel. Even when the first and second fuels are the same, the samples may be taken from the fuel at different points in production, transport, etc.

In some embodiments, the first material under test and second material under test may be different fuels or different fuel types. Examples of different fuel types that may be analyzed by the validation system described herein include, without limitation, gasoline, crude oil, natural gas, liquid gas, petroleum product blends, any other petroleum product, any other petroleum by-product, any product or combination of products having an acceptable RVP (or other property) defined by one or more of governmental and internal regulations, and combinations thereof.

As used herein, the term "controller" can include a PLC, DCS, or any other type of local or remote controller or collection of controllers. Moreover, although embodiments of the present disclosure are described in connection with a PLC as a controller, it should be appreciated that any type of hardware device and/or software can be used to perform the functions of the controller described herein.

In particular, it should be appreciated that the functions described herein may be performed by hardware components or may be embodied in sequences of machine-executable instructions, which may be used to cause a machine, such as a general-purpose or special-purpose processor or microprocessor (e.g., GPU or CPU) or logic circuits programmed with the instructions to perform the methods (FPGA). These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

More specifically, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as a non-transitory storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The Summary is neither intended or should it be construed as being representative of the full extent and scope of the present invention. The present disclosure is set forth in various levels of detail and the Summary as well as in the attached drawings and in the detailed description of the disclosure and no limitation as to the scope of the present disclosure is intended by either the inclusion or non inclusion of elements, components, etc. in the Summary. Additional aspects of the present disclosure will become more readily apparent from the detailed description, particularly when taken together with the drawings.

DETAILED DESCRIPTION

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

Figure 1:
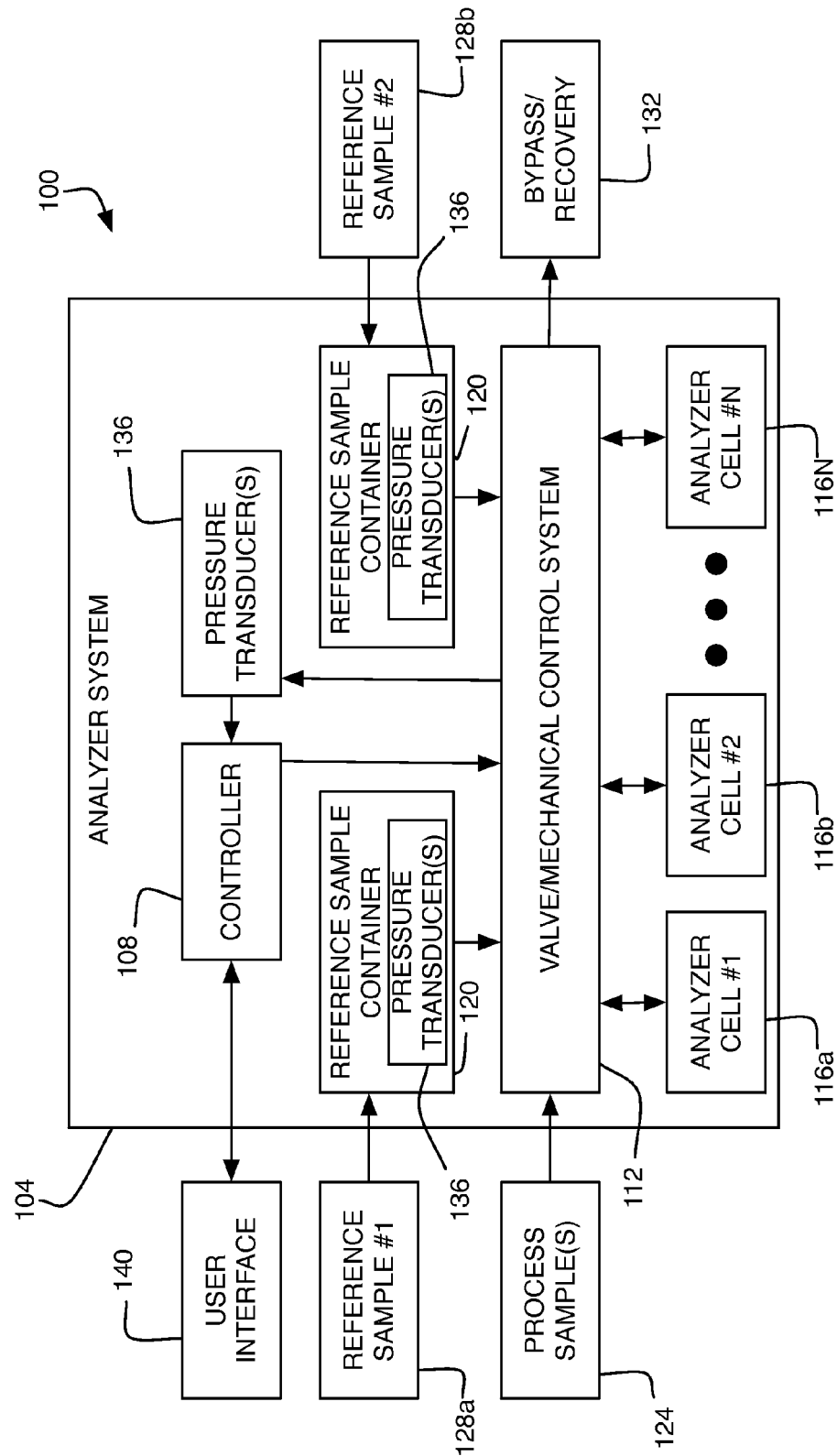
FIG. 1 depicts a validation/testing system in accordance with embodiments of the present disclosure.

With reference initially to FIG. 1, a validation/testing system 100 will be described in accordance with at least some embodiments of the present disclosure. The system 100 is shown to include an analyzer system 104 having a controller 108, a valve/mechanical control system 112, a plurality of analyzer cells 116*a*-N, one or more reference sample containers 120, and one or more pressure transducers 136, which may be separate from and/or integrated into the one or more reference sample containers 120. It should be appreciated that while the components of the analyzer system 104 are depicted as being co-located within the analyzer system 104, embodiments of the present disclosure are not so limited. For instance, one or more components depicted as being included in the analyzer system 104 may be located remote from the analyzer system 104. As a more specific, but non-limiting example, some or all of the functions executed by the controller 108 may be executed separate from the analyzer system 104 and the remotely-located controller 108 may be configured to interact with other components of the analyzer system 104 via a wired and/or wireless interface and/or other electro-mechanical systems. Furthermore, one or more of the components depicted in FIG. 1 may be combined or functions of multiple components may be integrated into a single component without departing from the scope of the present disclosure.

The controller 108 may include any electrical, mechanical, electro-mechanical, software, and/or hardware system that controls one or more functions of the analyzer system 104. In particular, the controller 108 may be configured to control the various operations of the analyzer system 104 via the valve/mechanical control system 112. In some embodiments, the controller 108 may comprise a PLC, microprocessor, firmware, software, FPGA, variants thereof, and/or combinations thereof. The controller 108 may be configured to interact and control one or more components of the valve/mechanical control system 112 so as to control the flow of process sample(s) 124 and/or reference samples 128*a*, 128*b* into and out of the analyzer cells 116*a*-N. Moreover, the controller 108 may be configured to control the valve/mechanical control system 112 so as to direct the flow of process sample(s) 124 and/or reference samples 128, 128*b* from an analyzer cell 116*a*-N to a bypass/recovery 132.

In some embodiments, the valve/mechanical control system 112 may comprise one or more pipes, tubes, pressure regulators, pressure reducers, pressure gauges, filters, ball valves, three-way valves, and combinations thereof. Of course, the valve/mechanical control system 112 may be configured to accommodate the types of samples 124, 128*a*, 128*b* being tested and/or validated.

Examples of process sample(s) 124 that may be introduced to analyzer cells 116*a*-N for analysis include, without limitation, gasoline, crude oil, natural gas, liquid gas, petroleum product blends, any other petroleum product, any other petroleum by-product, any gas, any combination of gases, any liquid, any combination of liquids, or combinations thereof. Additionally, although a single process sample box is depicted, it should be appreciated that the analyzer system 104 may be configured to receive a plurality of different process samples from different locations or sources. For example, a first process sample 124 may be provided to an analyzer cell 116 for analysis from a first processing stage and a second process sample 124 may be provided to an analyzer cell 116 (different or the same as the analyzer cell that receives the first process sample 124) for analysis. The first process sample 124 may be the same type of material or product as the second process sample 124 or the process samples may be different types of materials or products. Furthermore, the first and second process samples may be received from the same source, but at different times. In short, the analyzer system 104 is configured with a plurality of analyzer cells 116*a*-N to analyze one or more process samples 124, which may or may not be from the same source.

In addition to having the ability to test a plurality of different process samples 124 with its various analyzer cells 116*a*-N, the analyzer system 104 may also be configured to test or validate with one or more different reference samples 128*a*, 128*b*. As with the process samples 124, although two different reference samples 128*a*, 128*b* are depicted in FIG. 1, it should be appreciated that the analyzer system 104 may be configured to receive and validate/test with one, two, three, four, five, . . . , ten, or more different reference samples. The analyzer system 104 may have a dedicated integral reference sample container for each of the reference samples 128*a*, 128*b* or reference sample containers may be configured to receive a plurality of different reference samples. Suitable, but non-limiting examples, of reference samples 128*a*, 128*b* that may be utilized by the analyzer system 104 include Neohexane, gasoline, and any other reference sample known in the art.

Each reference sample may enter the analyzer system 104 and be held therein by a reference sample container 120. A non-limiting example of a reference sample container 120 is a constant pressure sample cylinder manufactured and distributed by Welker under one of part numbers CP2, CP30A, or the like. The reference sample container 120 can be configured to provide some of a reference sample 128*a*, 128*b* to an analyzer cell 116*a*-N via the valve/mechanical control system 112, based on the controller's 108 actuation of the valve/ mechanical control system 112. Thus, the controller 108 can be configured to cause process samples 124 to enter an analyzer cell 116a-N as well as cause reference samples 128a, 128b to enter an analyzer cell 116a-N for analysis, validation, testing, etc.

The analyzer cells 116a-N may be of the same or different types. As some non-limiting examples, the analyzer cells 116a-N may each be configured to test the same property (e.g., vapor pressure) or properties of a process sample 124 or reference sample 128a, 128b. In alternative embodiments, some of the analyzer cells 116a-N may be configured to analyze one property or subset of properties of a sample 124, 128a, 128b whereas others of the analyzer cells 116a-N may be configured to analyze a different property or subset of properties of a sample 124, 128a, 128b. In some embodiments, one, some or all of the analyzer cells 116a-N may correspond to RVP analyzer cells. In some embodiments, one, some, or all of the analyzer cells 116a-N may correspond to other types of analyzer cells such as chromatographs, sulfur analyzers, other types of vapor pressure analyzers, and the like.

As shown in FIG. 1, the valve/mechanical control system 112 can be used to carry samples 124, 128a, 128b to the analyzer cells 116a-N and from the analyzer cells 116a-N to a bypass/recovery 132. The samples 124, 128a, 128b may be maintained in an analyzer cell 116a-N for a predetermined amount of time (e.g., during an analysis period) and then purged from the analyzer system 104 to the bypass/recovery 132.

The pressure transducer(s) 136 provide a mechanism that enables the controller 108 to monitor and determine the various pressures within the valve/mechanical control system 112. It should be appreciated that one or more pressure transducers 136 may also be connected between the analyzer cells 116a-N and controller 108, thereby enabling the controller 108 to monitor and determine pressures within the analyzer cells. It should be appreciated that any type of known or yet to be developed pressure transducer may be used for the pressure transducer(s) 136. It should also be appreciated that pressure gauges may be used instead of or in addition to pressure transducers. The pressure gauges may or may not necessarily be configured to provide inputs to controller 108.

The controller 108 may also be configured to provide outputs and receive inputs from a user interface 140. The user interface 140 may be remotely located from the controller 108 (e.g., there may be a communication network between the user interface 140 and controller 108). Alternatively or additionally, the user interface 140 may be located next to or proximate with the controller 108. As a non-limiting example, the user interface 140 may correspond to an HMI for a PLC. Other types of interfaces including computer interfaces, mobile phone interfaces, Personal Digital Assistant (PDA) interfaces, etc. can also be used as the user interface 140.

In addition to interfacing with the user interface 140, the controller 108 may also be configured to interface with one or more automated mechanisms. For instance, the controller 108 may be configured to generate alerts, alarms, analysis reports, etc. via communications with one or more automated computing machines (e.g., servers). Thus, the analysis performed by the analyzer system 104 can be provided as an output via the user interface 140 and/or as an output to an automated computing machine that further processes the information received from the controller 108.

In some embodiments, an automated feedback loop may be controlled based on inputs from the controller 108. More specifically, the controller 108 may be configured to provide outputs to a process system that is providing the process sample(s) 124 to the analyzer system 104. If the controller 108 determines that the process sample(s) 124 are failing to meet a certain quality threshold (e.g., vapor pressure is above or below a predetermined threshold), the controller 108 may automatically instruct the processing system to alter its processing tolerances to bring the process sample(s) 124 back into compliance with the predetermined threshold(s). Thus, the analyzer system 104 can enable a processing system to automatically and immediately adjust its process to ensure that the output of the processing system is continuously meeting quality requirements. Of course, adjustments made by the processing system based on inputs received from the controller 108 may be verified or confirmed by a system administrator prior to the processing system implementing the adjustment.

Figure 2:
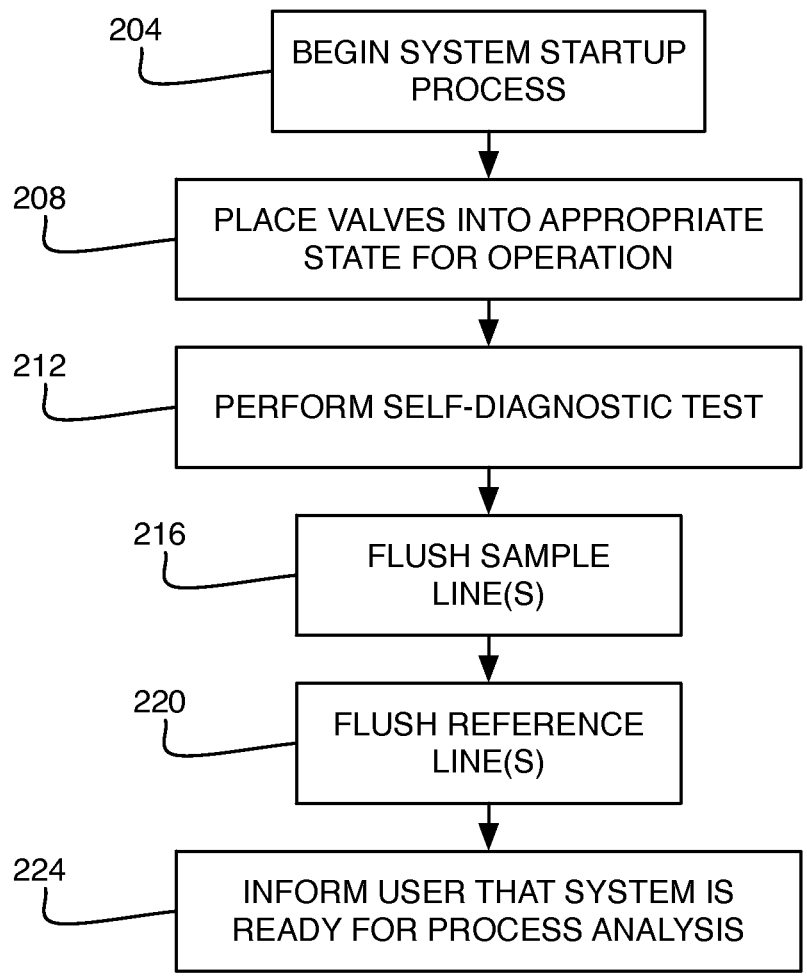
FIG. 2 depicts a system startup method in accordance with embodiments of the present disclosure.

With reference now to FIG. 2, a startup process for the analyzer system 104 will be described in accordance with at least some embodiments of the present disclosure. The process begins in step 204 and continues by placing the valves and other mechanical/fluid control mechanisms into their appropriate state for operation (step 208). This step of initializing or verifying the initialization of the valve/mechanical control system 112 may involve automatically or manually adjusting one or more valves to their appropriate state (e.g., open, closed, partially open, etc.).

The method continues with the controller 108 performing a self-diagnostic test that confirms the valve/mechanical control system 112 has been initialized properly (step 212). In particular, the controller 108 may utilize inputs from one or more pressure transducers 136 to determine whether the valves and other mechanisms in the valve/mechanical control system 112 are in the appropriate state. The controller 108 may also confirm that all analyzer cells 116a-N are clear and the reference sample containers 120 are filled with the appropriate reference samples, if necessary. The controller 108 may further confirm that it is operating correctly by testing one or more of its own functions.

After the self-diagnostic test has been completed, the process continues with the controller 108 flushing the sample lines that provide the process sample(s) 124 to the analyzer cells 116a-N (step 216). The controller 108 then flushes the lines that carry reference samples to the analyzer cells 116a-N (step 220). In these steps, the lines of the valve/mechanical control system 112 may be flushed with any type of cleaning or neutral agent.

After the lines have been appropriately flushed, the controller 108 provides an output to the user interface 140 indicating that the analyzer system 104 is ready for process analysis (step 224). Alternatively or additionally, the controller 108 may automatically begin process analysis.

Figure 3:
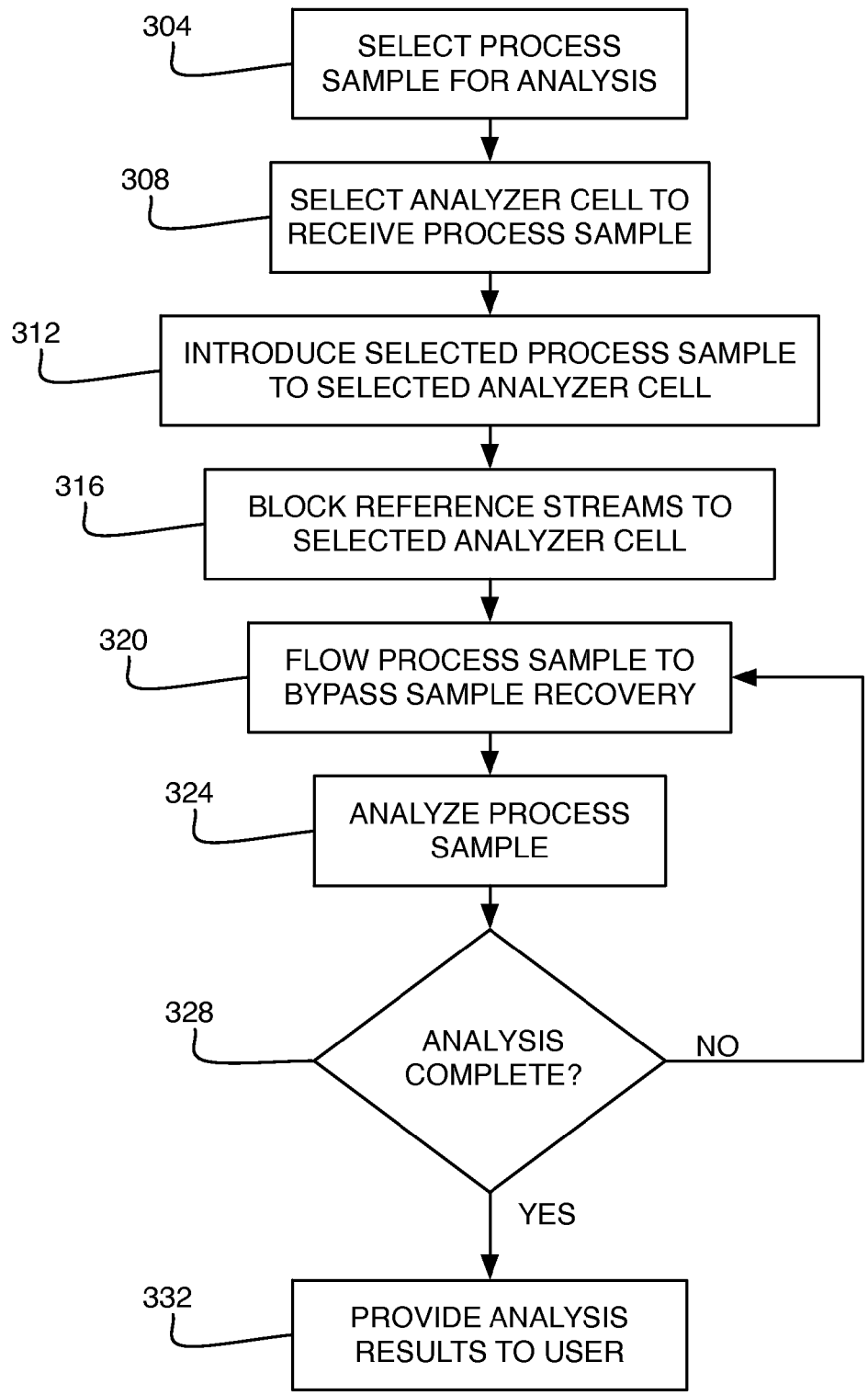
FIG. 3 depicts a sample analysis method in accordance with embodiments of the present disclosure.

With reference now to FIG. 3, a method of performing an analysis of one or more process samples 124 will be described in accordance with at least some embodiments of the present disclosure. While the analysis method is described in connection with analyzing a single process sample, it should be appreciated that embodiments of the present disclosure are not so limited. In particular, the method depicted in FIG. 3 may be performed sequentially or simultaneously for a plurality of process samples, each of which may be provided to the same or different analyzer cells 116a-N.

The method begins with the controller 108 selecting a process sample 124 for analysis (step 304). The process sample 124 may be selected automatically or manually (e.g., with user input). The controller 108 may also select the analyzer cell 116a-N that will receive the selected process sample 124 (step 308). In this step, the controller 108 may select the appropriate lines/valves to provide the selected process sample 124 to the selected analyzer cell 116.

Once the process sample and analyzer cell have been selected, the method continues with the controller 108 controlling the valve/mechanical control system 112 so as to introduce the selected process sample 124 to the selected analyzer cell 116 (step 312). The controller 108 may also control the valve/mechanical control system 112 such that the reference samples 128a, 128b are prohibited from reaching the selected analyzer cell 116 at least during the analysis of the selected process sample (step 316).

Thereafter, the controller 108 causes the selected process sample 124 to flow through the selected analyzer cell 116 and then to the bypass/recovery 132 (step 320). While the selected process sample 124 is flowing to bypass/recovery 132, the process sample 124 is analyzed within the selected analyzer cell 116 (step 324). If the analysis of the process sample 124 is not complete (step 328), then steps 320 and 324 continue to be executed. Once the analysis of the process sample 124 is complete, the results of the analysis are output by the controller 108 (step 332). In some embodiments, the controller 108 outputs some or all of the results of the analysis via the user interface 140.

Figure 4:
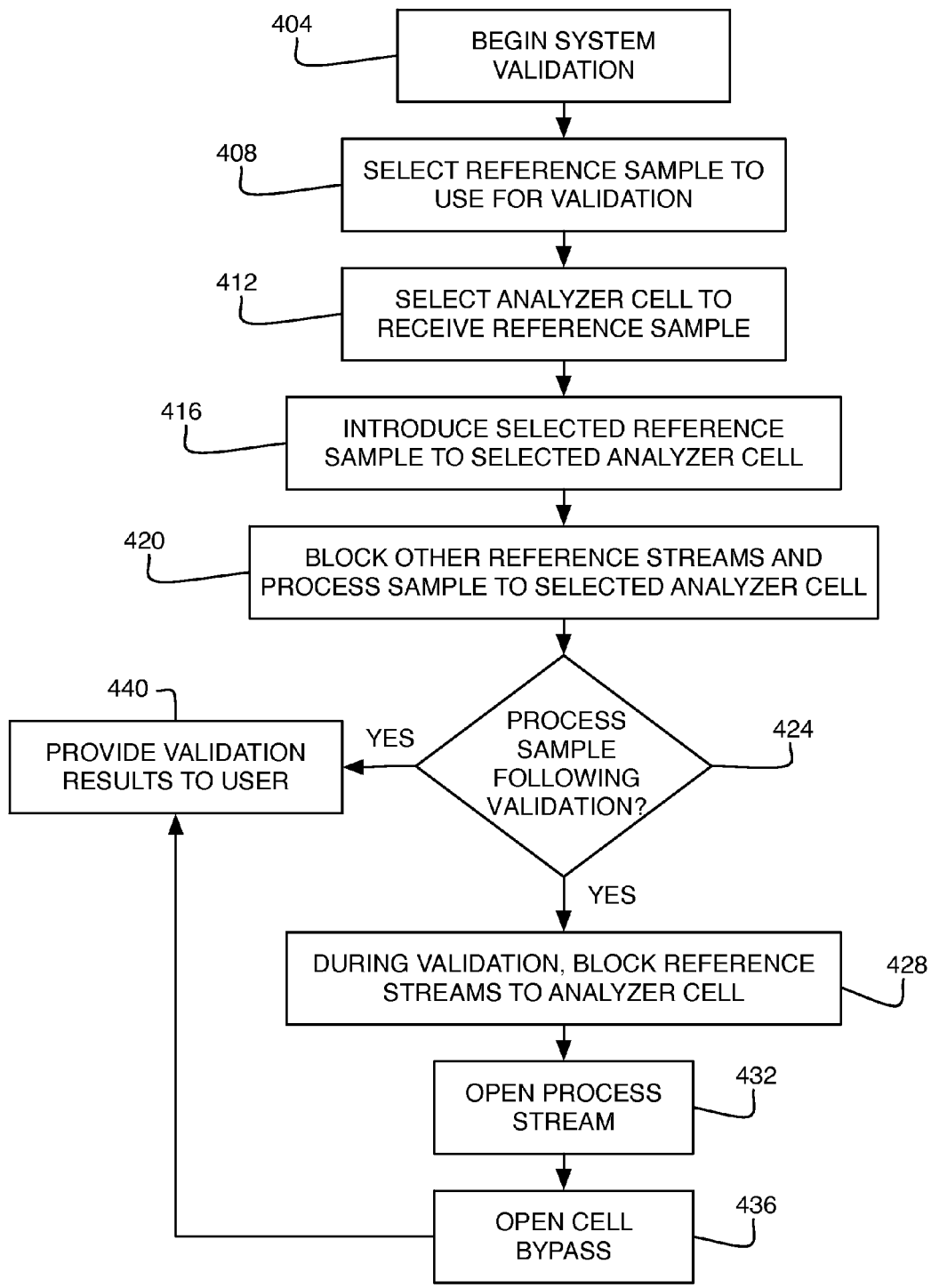
FIG. 4 depicts a system validation method in accordance with embodiments of the present disclosure.

With reference now to FIG. 4, a method of performing system validation will be described in accordance with embodiments of the present disclosure. As with FIG. 3, while the validation method is described in connection with using a single reference sample, it should be appreciated that embodiments of the present disclosure are not so limited. In particular, the method depicted in FIG. 3 may be performed sequentially or simultaneously for a plurality of process samples, each of which may be provided to the same or different analyzer cells 116a-N.

The method begins either in response to an appropriate user input at the user interface 140 or in response to detecting one or more predetermined conditions (step 404). Thereafter, a reference sample 128a, 128b is selected for use in the validation process (step 408). The controller 108 then selects an analyzer cell 116 to receive the selected reference sample 128 (step 412).

After the controller 108 has made the appropriate selections, the method continues with the controller 108 controlling the valve/mechanical control system 112 so as to introduce the selected reference sample 128 to the selected analyzer cell 116 (step 416). The reference sample 128 may be provided directly from an external source to an analyzer cell 116 or it may be provided from a reference sample container 120. The controller 108 may also control the valve/mechanical control system 112 such that the non-selected reference samples and the process sample 124 are prohibited from reaching the selected analyzer cell 116 at least during an introduction of the reference sample to the selected analyzer cell (step 420).

Thereafter, it is determined whether or not a process sample will be provided to the selected analyzer cell 116 after the validation is completed (step 424). If this query is answered affirmatively, then the controller 108 will continue to block the non-selected reference samples from reaching the analyzer cell 116 (step 428), but a process sample is allowed to flow through the valve/mechanical control system 112 (step 432) to the bypass/recovery 132 (step 436). This continues for the duration of the validation with the reference sample.

Thereafter, or if the query of step 424 is answered negatively, then the validation results are collected by the controller 108 and distributed accordingly (step 440). In some embodiments, the controller 108 may provide the validation results to a user via the user interface 140.

Figure 5:
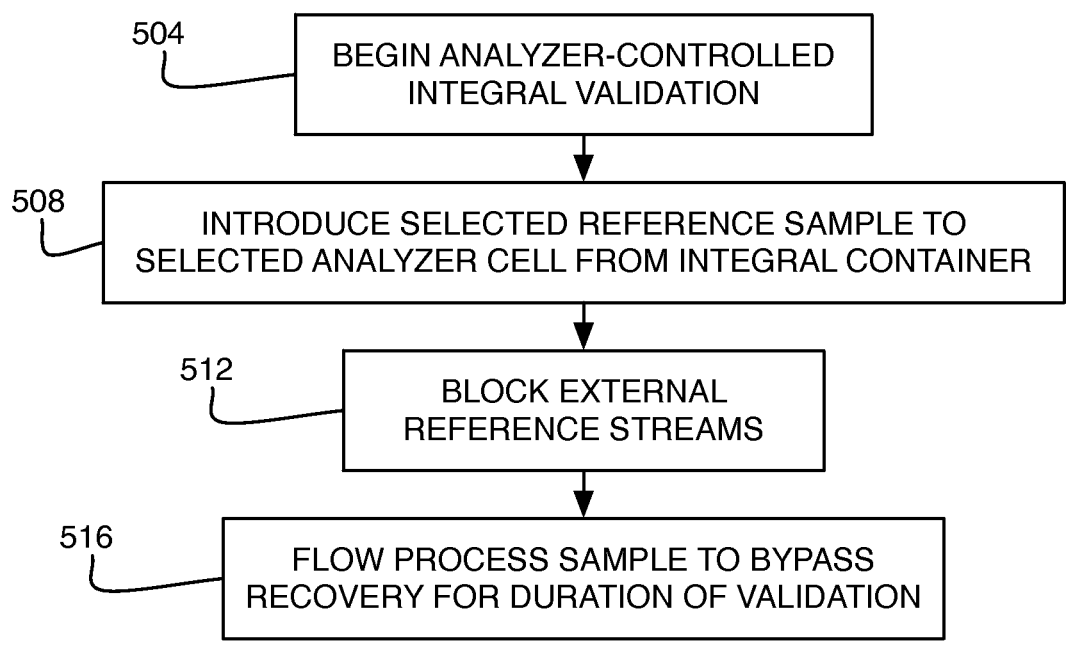
FIG. 5 depicts an analyzer-controlled integral validation method in accordance with embodiments of the present disclosure.

With reference now to FIG. 5, a method of performing an analyzer/controlled integral validation method will be described in accordance with at least some embodiments of the present disclosure. The method begins in step 504 and continues with the controller 108 selecting a reference sample from an integral reference sample container 120 and providing the selected reference sample to a selected analyzer cell 116 (step 508). In this step, the controller 108 may control the operations of the valve/mechanical control system 112 so that the selected reference sample flow from the reference sample container 120 to the selected analyzer cell 116. The controller 108 may also control the valve/mechanical control system 112 such that the non-selected reference samples are prohibited from reaching the selected analyzer cell 116 (step 512).

While the validation is performed on the reference sample with the analyzer cell 116, process sample is allowed to flow to the bypass/recovery 132 (step 516). The flowing of the process sample to the bypass/recovery 132 during the analyzer-controlled integral validation optimizes the system response time (e.g., minimizes the amount of time for the validation and minimizes the amount of time between the validation and testing of a new process sample).

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor (GPU or CPU) or logic circuits programmed with the instructions to perform the methods (FPGA). These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While illustrative embodiments of the disclosure have been described in detail herein, it is to be understood that the inventive concepts may be otherwise variously embodied and employed, and that the appended claims are intended to be construed to include such variations, except as limited by the prior art.

What is claimed is:

1. A validation system, comprising:
    a valve and mechanical control system, including:
        a set of valves dedicated to analyzers in an analyzer system;
        one or more pressure and flow instruments configured to ensure process and validation samples are supplied to the analyzers of the analyzer system under stable and consistent conditions;
        solenoid-operated valves and interconnections configured to enable stream selection;
        one or more constant pressure cylinders configured to contain one or more reference samples, respectively;
        one or more motive gas controls configured to operate at least one of the constant pressure cylinders and solenoid-operated valves; and
    a controller configured to manage operations of the valve and mechanical control system, wherein the valve and mechanical control system interfaces the validation system to a first analyzer cell and a second analyzer cell, wherein the first cell comprises a first RVP cell configured to analyze an RVP of a first reference sample received from the validation system and wherein the second cell comprises a second RVP cell configured to analyze an RVP of a second sample.

2. The system of claim 1, wherein the set of valves comprise double block and bleed valves and three-way valves.

3. The system of claim 1, wherein the controller comprises at least one of a PLC, DCS, microcontroller, and CPU.

4. The system of claim 1, wherein the controller is configured to provide a plurality of different reference samples to each analyzer in the analyzer system.

5. The system of claim 4, wherein a first reference sample in the plurality of different reference samples comprises a first fuel type and a second reference sample in the plurality of different reference samples comprise a second different fuel type.

6. The system of claim 5, wherein at least one of the first and second reference samples comprise at least one of gasoline, crude oil, natural gas, liquid gas, petroleum product blends, a petroleum product, a petroleum by-product, and a product or combination of products having an acceptable RVP defined by one or more of governmental and internal regulations.

7. The system of claim 6, wherein at least one of the first and second reference samples comprise at least one of gasoline, Neohexane or N-Pentane and wherein the at least one of the first and second reference samples is used to validate analyzers in the analyzer system.

8. The system of claim 7, wherein the analyzers comprise a first analyzer cell and a second analyzer cell and each of the first and second analyzer cell are configured to be validated by the validation system with reference samples provided by the validation system.

9. The system of claim 8, wherein the first analyzer cell corresponds to a cell of at least one of a gas chromatograph and a sulfur analyzer and wherein the second analyzer cell corresponds to a cell of at least one of the gas chromatograph and the sulfur analyzer.

10. A validation system, comprising:
    a valve and mechanical control system, including:
        a set of valves dedicated to analyzers in an analyzer system;
        one or more pressure and flow instruments configured to ensure process and validation samples are supplied to the analyzers of the analyzer system under stable and consistent conditions;
        solenoid-operated valves and interconnections configured to enable stream selection;
        one or more constant pressure cylinders configured to contain one or more reference samples, respectively;
        one or more motive gas controls configured to operate at least one of the constant pressure cylinders and solenoid-operated valves; and
    a controller configured to manage operations of the valve and mechanical control system, wherein the controller is configured to cause the valve and mechanical control system to simultaneously provide reference samples to a first and second analyzer in the analyzer system, wherein the first analyzer receives a first reference sample from a first reference sample container and wherein the second analyzer receives a second reference sample from a second reference sample container that is different from the first reference sample container.

11. The system of claim 1, wherein the controller is configured to allow a process sample to become its own standard for future analyzer validations.

* * * * *